(12) United States Patent
Pacetti

(10) Patent No.: US 7,871,658 B2
(45) Date of Patent: Jan. 18, 2011

(54) STENT COATING METHOD

(75) Inventor: Stephen Dirk Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 400 days.

(21) Appl. No.: 12/027,084

(22) Filed: Feb. 6, 2008

(65) Prior Publication Data

US 2008/0124451 A1    May 29, 2008

Related U.S. Application Data

(62) Division of application No. 10/606,712, filed on Jun. 26, 2003, now Pat. No. 7,341,630.

(51) Int. Cl.
| B05B 1/28 | (2006.01) |
| B05B 7/06 | (2006.01) |
| B05B 13/02 | (2006.01) |
| A61L 33/00 | (2006.01) |
| B05D 1/02 | (2006.01) |
| B05D 1/34 | (2006.01) |

(52) U.S. Cl. ............... 427/2.1; 427/2.24; 427/2.25; 427/421.1; 427/426; 118/313; 118/320; 239/290; 239/294; 239/296

(58) Field of Classification Search ............... 427/2.1, 427/2.24, 2.25, 421.1, 426; 239/290, 294, 239/296; 118/313
See application file for complete search history.

(56) References Cited

U.S. PATENT DOCUMENTS

| 2,373,595 A | 4/1945 | Peeps |
| 3,049,439 A | 8/1962 | Coffman |
| 3,232,540 A | 2/1966 | Cassanmangnago |
| 3,848,807 A | 11/1974 | Partida |
| 4,733,665 A | 3/1988 | Palmaz |
| 4,743,252 A | 5/1988 | Martin et al. |
| 4,800,882 A | 1/1989 | Gianturco |
| 4,886,062 A | 12/1989 | Wiktor |
| 4,967,606 A | 11/1990 | Wells et al. |
| 5,015,505 A | 5/1991 | Cetnar |
| 5,075,138 A | 12/1991 | Tanaka et al. |

(Continued)

FOREIGN PATENT DOCUMENTS

JP    2003211063    7/2003

(Continued)

OTHER PUBLICATIONS

English Translated Abstract of JP 2003211063A, Jul. 2003.

(Continued)

*Primary Examiner*—Timothy H Meeks
*Assistant Examiner*—Cachet I Sellman
(74) *Attorney, Agent, or Firm*—Squire, Sanders & Dempsey, L.L.P.

(57) ABSTRACT

A system, nozzle assembly, and method for coating a stent with a solvent and polymer are provided. The polymer can include a therapeutic substance or a drug. The polymer and solvent can be discharged from separate tubes disposed within another tube carrying moving air. The polymer and the solvent mix together when they are discharged and are atomized by the air. The ends of the tubes can be concentric with each other.

16 Claims, 4 Drawing Sheets

U.S. PATENT DOCUMENTS

| | | | |
|---|---|---|---|
| 5,225,750 A | 7/1993 | Higuchi et al. | |
| 5,249,746 A | 10/1993 | Kaneko et al. | |
| 4,733,665 A | 1/1994 | Palmaz | |
| 5,368,560 A | 11/1994 | Rambo et al. | |
| 5,435,491 A | 7/1995 | Sakuma | |
| 5,437,889 A | 8/1995 | Jones | |
| 5,447,567 A * | 9/1995 | Tanaka et al. | 118/303 |
| 5,464,650 A | 11/1995 | Berg et al. | |
| 5,511,726 A | 4/1996 | Greenspan et al. | |
| 5,527,337 A | 6/1996 | Stack et al. | |
| 5,662,922 A | 9/1997 | Christensen | |
| 5,700,286 A | 12/1997 | Tartaglia et al. | |
| 5,713,949 A | 2/1998 | Jayaraman | |
| 5,741,554 A | 4/1998 | Tisone | |
| 5,766,710 A | 6/1998 | Turnlund et al. | |
| 5,769,883 A | 6/1998 | Buscemi et al. | |
| 5,810,254 A | 9/1998 | Kropfield | |
| 5,824,056 A | 10/1998 | Rosenberg | |
| 5,837,313 A | 11/1998 | Ding et al. | |
| 5,843,172 A | 12/1998 | Yan | |
| 5,869,127 A | 2/1999 | Zhong | |
| 5,873,904 A | 2/1999 | Ragheb et al. | |
| 5,957,899 A | 9/1999 | Spears et al. | |
| 5,980,972 A | 11/1999 | Ding | |
| 5,984,449 A | 11/1999 | Tajika et al. | |
| 6,056,993 A | 5/2000 | Leidner et al. | |
| 6,096,070 A | 8/2000 | Ragheb et al. | |
| 6,121,027 A | 9/2000 | Clapper et al. | |
| 6,132,809 A | 10/2000 | Hynes et al. | |
| 6,143,370 A | 11/2000 | Panagiotou et al. | |
| 6,209,621 B1 | 4/2001 | Treacy | |
| 6,214,407 B1 | 4/2001 | Laube et al. | |
| 6,224,675 B1 | 5/2001 | Prentice et al. | |
| 6,395,326 B1 | 5/2002 | Castro et al. | |
| 6,462,284 B1 | 10/2002 | Hashimoto | |
| 6,491,666 B1 | 12/2002 | Santini, Jr. et al. | |
| 6,503,954 B1 | 1/2003 | Bhat et al. | |
| 6,562,136 B1 | 5/2003 | Chappa et al. | |
| 6,767,637 B2 * | 7/2004 | Park et al. | 428/402.21 |
| 6,969,012 B2 * | 11/2005 | Kangas et al. | 239/400 |
| 7,338,557 B1 * | 3/2008 | Chen et al. | 118/300 |
| 7,341,630 B1 | 3/2008 | Pacetti | |
| 7,345,480 B2 | 3/2008 | Pai et al. | |
| 7,354,480 B1 | 4/2008 | Kokish et al. | |
| 7,390,523 B2 | 6/2008 | Pacetti et al. | |
| 2003/0099765 A1 | 5/2003 | Jayaraman | |
| 2003/0143315 A1 * | 7/2003 | Pui et al. | 427/2.1 |
| 2003/0196595 A1 | 10/2003 | Takeshita et al. | |

FOREIGN PATENT DOCUMENTS

WO      WO 98/23228      6/1998

OTHER PUBLICATIONS

"Impulse Jetting: About Us," http://www.impulsejetting.com/about.html, printed Dec. 18, 2000 (1 page).

"Impulse Jetting: Our Technology," http://www.impulsjetting.com/tech1.html, printed Dec. 18, 2000 (1 page).

Trident, Inc., http://www.tridetintl.com/subbody.html, printed Sep. 18, 2003 (1 page).

World Precision Instruments, Inc., "Nanolite Injector," http://www.wpiinc.com/WPI_Web/Microinjection/Nanoliter_Injector.html , printed Sep. 18, 2003 (2 pages).

World Precision Instruments, Inc., "Pneumatic PicoPumps," httm://www.wpi-europe.com/pumps/Pneumatic_PicoPumps.html, printed Sep. 18, 2003 (5 pages).

World Precision Instruments, Inc., "Nanoliter 2000," http://www.wpi-europe.com/pumps/Nanoliter_Injector.html, printed Sep. 18, 2003 (3 pages).

World Precision Instruments, Inc., http://www.wpiinc.com/WPI_Web/Pumps/pneumatic_Fig.gif, printed Sep. 30, 2002 (1 page).

World Precision Instruments, Inc., "Pneumatic PicoPumps," http://www.wpiinc.com/WPI_Web/Microinjection/Pneumatic_PicoPumps.html , printed Sep. 18, 2003 (4 pages).

* cited by examiner

STENT COATING METHOD

This application is a divisional application of U.S. application Ser. No. 10/606,712, filed Jun. 26, 2003 now U.S. Pat. No. 7,341,630, which is incorporated herein by reference in its entirety.

TECHNICAL FIELD

This invention relates to an apparatus used in the process of coating a stent, and more particularly provides a nozzle for use in drug eluting stent spray coating.

BACKGROUND

Blood vessel occlusions are commonly treated by mechanically enhancing blood flow in the affected vessels, such as by employing a stent. Stents act as scaffolding, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Giantur co, and U.S. Pat. No. 4,886,062 issued to Wiktor.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by spraying the composition onto the stent. The solvent is allowed to evaporate, leaving on the stent surfaces a coating of the polymer and the therapeutic substance impregnated in the polymer.

However, a shortcoming of the above-described method of medicating a stent is the potential for clogging of a spray nozzle used to the coat the stent. The clogging is caused by accumulation of solid polymer on and around the nozzle tip from which the polymer solution exits. The clogging can lead to a drift in the flow rate, which in turn leads to a variation in total drug content from stent to stent, a variation in the drug release rate from stent to stent, and non-uniform coating of the stents.

Accordingly, a new nozzle for spraying coating is needed to minimize nozzle blockage and the associated variability in the coating behavior.

SUMMARY

Briefly and in general terms, the present invention is directed to a method of coating a stent. In aspects of the present invention, the method comprises positioning a nozzle assembly relative to a stent, the nozzle assembly having a first tube for discharging a composition including a polymer, a second tube, positioned over the first tube, for discharging a solvent free or substantially free from drugs or the polymer, and a third tube, positioned over the second tube, for discharging a gas. The method further comprises discharging the composition and the solvent from the nozzle assembly onto the stent so that the discharged composition and discharged solvent combine before contacting the stent, and expelling the gas from the third tube so that the discharged solvent and the discharged composition are atomized by the gas into droplets.

In further aspects, the solvent and the polymer composition are discharged at different rates. In detailed aspects, the composition additionally includes a drug.

In other aspects of the present invention, the method comprises discharging a composition including a polymer out from an end segment of a first tube and toward a stent and discharging a solvent out from an end segment of a second tube, the solvent being free or substantially free from drugs or the polymer, the end segment of the second tube disposed adjacent the end segment of the first tube such that the discharged composition and the discharged solvent combine before contacting the stent. The method further comprises discharging gas out from an aperture formed in a third tube, the aperture having an annular shape that surrounds the end segment of the first tube and the end segment of the second tube such that the discharged composition and the discharged solvent are atomized by the discharged gas.

The features and advantages of the invention will be more readily understood from the following detailed description which should be read in conjunction with the accompanying drawings.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

Figure 1:
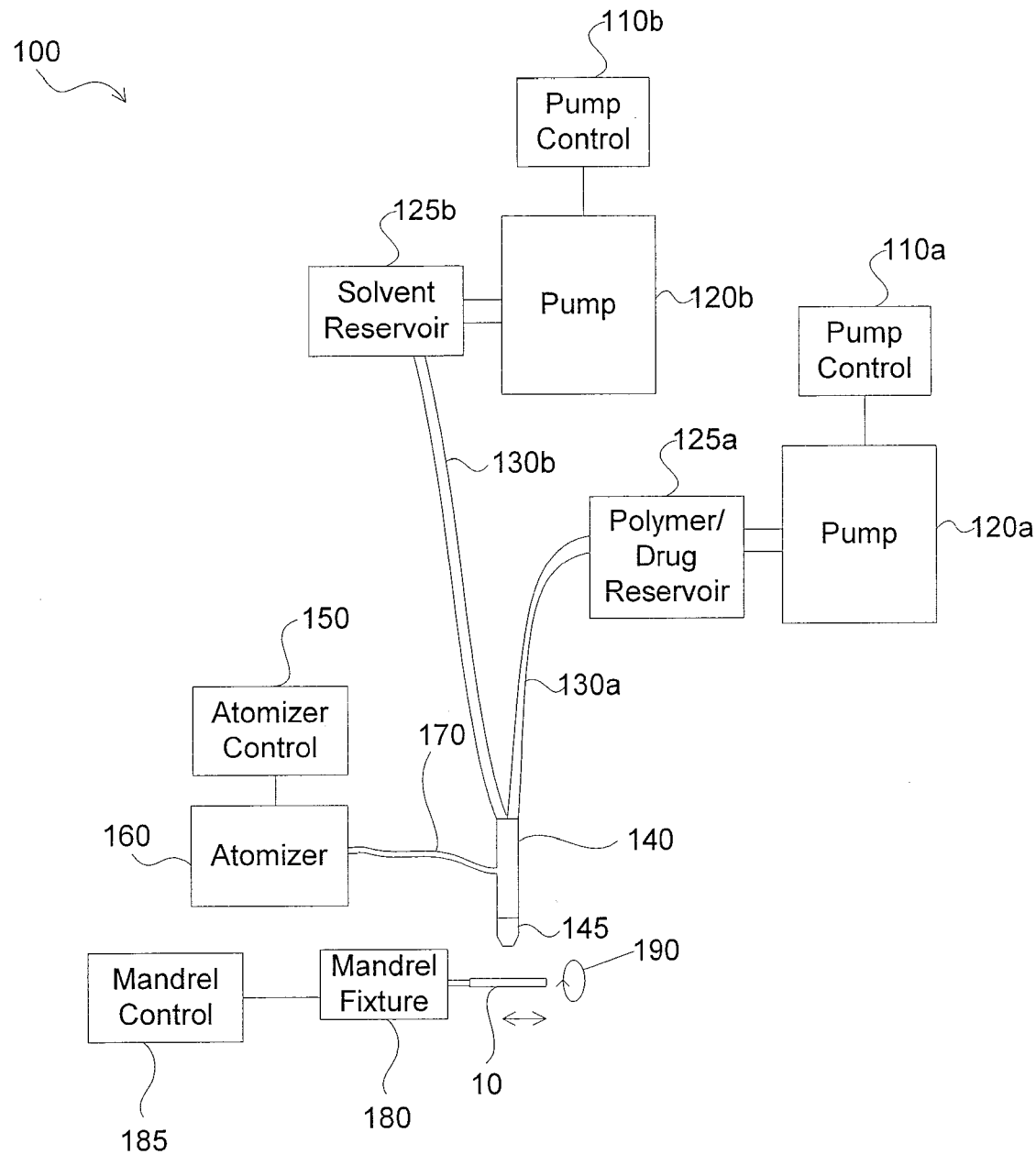
FIG. 1 is a block diagram illustrating a coating system for coating a stent with a composition.
Figure 2:
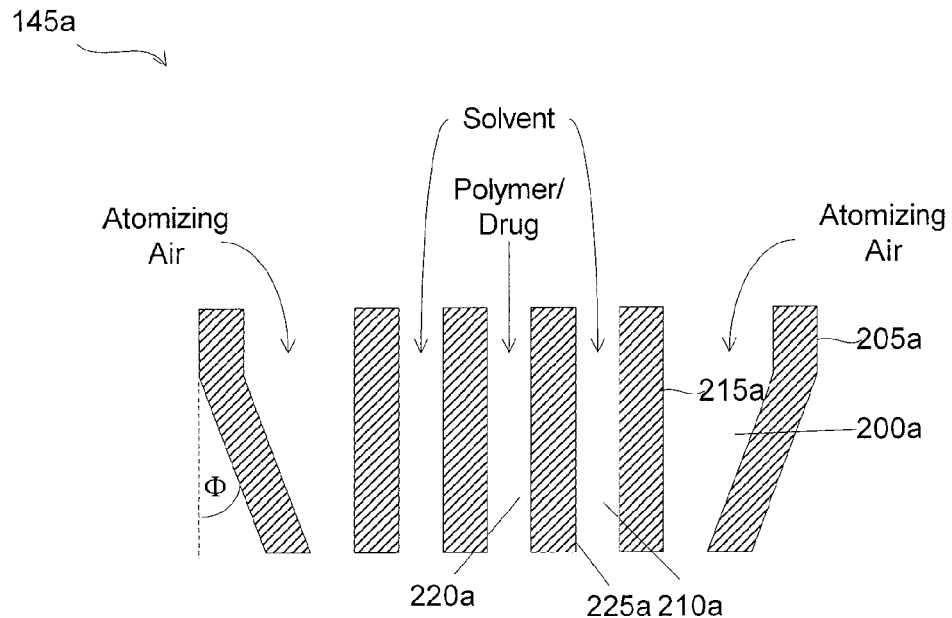
FIG. 2 is a cross section illustrating the nozzle tip of the coating system of FIG. 1 in accordance with an embodiment of the invention.
Figure 3:
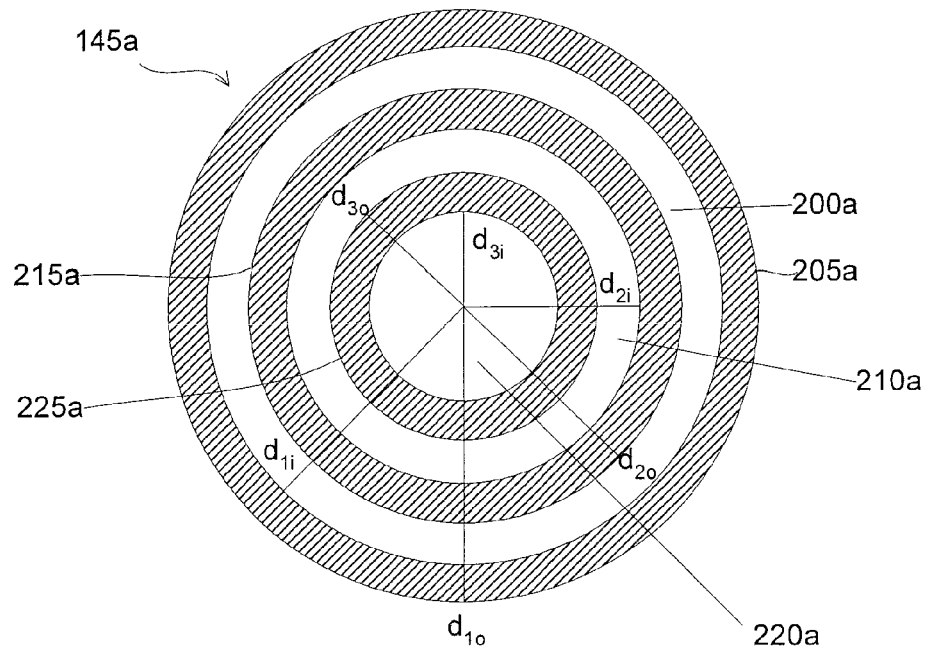
FIG. 3 is a bottom view of the nozzle tip of the nozzle tip of FIG. 1.
Figure 4:
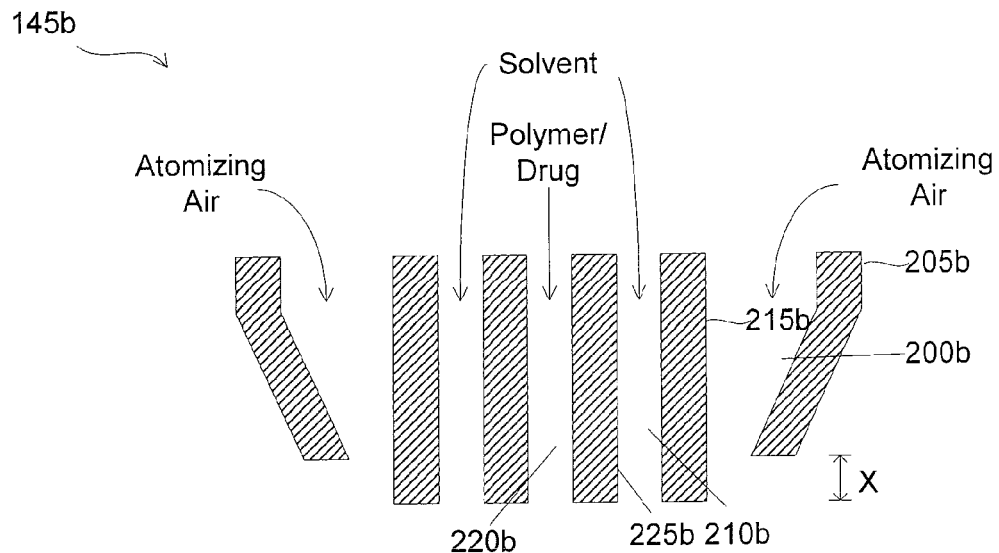
FIG. 4 is a cross section illustrating a nozzle tip according to a second embodiment of the invention.
Figure 5:
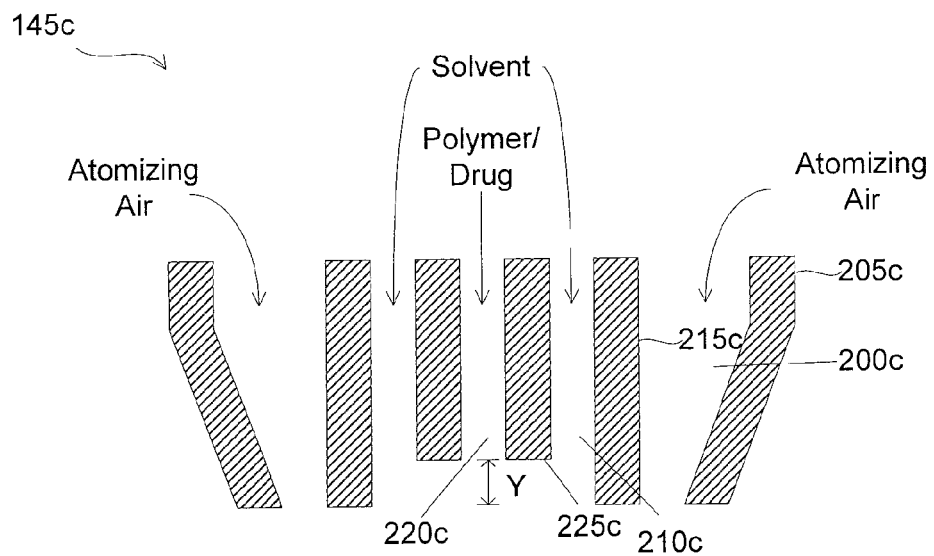
FIG. 5 is cross section illustrating a nozzle tip according to a third embodiment of the invention.
Figure 6:
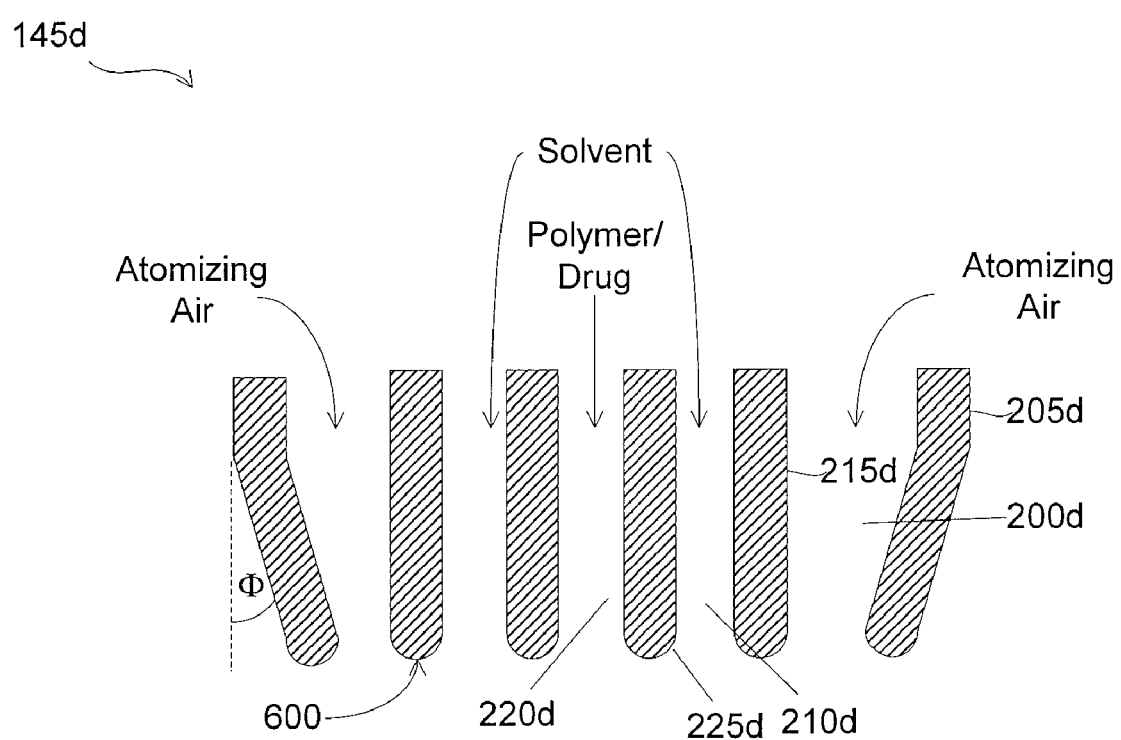
FIG. 6 is a cross section illustrating a nozzle tip according to a fourth embodiment of the invention.

FIG. 1 is a block diagram illustrating a coating system 100 for coating a stent 10 with a composition. The coating system 100 comprises pump controls 110a and 110b; pumps 120a and 120b; a polymer and/or drug reservoir 125a (referred to hereinafter as polymer/drug reservoir 125a), which may optionally include solvent(s) (for placing polymer and/or drug in a liquid composition form); a solvent reservoir 125b; a nozzle assembly 140 having a nozzle tip 145; an atomizer control 150; an atomizer 160; a mandrel fixture 180; and a mandrel fixture control 185. The pump control 110a is communicatively coupled to the pump 120a and controls the amount of polymer and/or drug dispensed by the pump 120a from the polymer/drug reservoir 125a. The pump control 110a may include mechanical and/or electrical control mechanisms. In an embodiment of the invention, the pump control 110a is integrated with the pump 120a. Similarly, the pump control 110b is communicatively coupled to the pump 120b and controls the amount of solvent dispensed by the pump 120b from the solvent reservoir 125b. The pump control 110b may include mechanical and/or electrical control mechanisms. In an embodiment of the invention, the pump control 110b is integrated with the pump 120b. In another embodiment of the invention, the pump controls 110a and 110b are combined into a single unit that controls the pumps 120a and 120b.

The pumps 120a and 120b pump a polymer/drug combination and a solvent from the reservoirs 125a and 125b respectively, for coating the stent 10 in situ, to the nozzle assembly 140 via a tubing 130a and 130b respectively. The pumps 120a and 120b may pump the contents of the reservoirs 125a and 125b at a rate of 0.15 cc/min, for example. In an embodiment of the invention, the pumps 120a and 120b can pump the contents of the reservoirs 125a and 125b, respectively, at different rates. Further, the pump 120b may alone pump solvent so as to clean the nozzle 140. In one embodiment of the invention, the pumps 120a and 120b include a syringe pumps. In another embodiment of the invention, the pumps 120a and 120b include a gear pumps. It will be appreciated that the pumps 120a and 120b can comprise other types of pumps and/or combinations of pumps such as positive displacement pumps, constant displacement pumps or green pumps.

Representative examples of polymers that can be used to coat a stent include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly (ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride, poly(vinylidene fluoride-co-hexafluoropropene), and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and/or the therapeutic substance and is capable of dissolving the polymer and/or therapeutic substance at the concentration desired. The solvent in the solvent reservoir 125b could be, in one embodiment, an excellent solvent for the polymer but a poor solvent for the therapeutic substance. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

The atomizer 160 supplies high-pressure air to the nozzle assembly 140 via a tubing 170. This high-pressure air is used to atomize the polymer/drug composition and the solvent dispensed from the nozzle assembly 140 onto the stent 10, as will be discussed in further detail below. The atomizer control 150 is communicatively coupled to the atomizer 160 and controls the pressure of the air dispensed from the atomizer 160 to the nozzle assembly 140. The atomizer control 150 can include electrical mechanisms, mechanical mechanisms, or a combination thereof to control the atomizer 160. In an embodiment of the invention, the atomizer control 150 and the atomizer 160 can be integrated into a single device. In another embodiment of the invention, the atomizer 160 can include an ultrasonic atomizer that uses ultrasound in place of atomizing air to atomize the polymer/drug composition and the solvent.

The mandrel fixture 180 supports the stent 10 during a coating application process. In addition, the mandrel fixture 180 can include an engine so as to provide rotational motion about the longitudinal axis of the stent 10, as depicted by the arrow 190, during the coating process. Another motor can also be provided for moving the stent 10 in a linear direction, back and forth. The mandrel control 185 is communicatively coupled to the mandrel fixture 180 and controls movement of the stent 10. The type of stent that can be crimped on the mandrel fixture 180 is not of critical significance. The term stent is broadly intended to include self- and balloon-type expandable stents as well as stent-grafts. It will be appreciated by one of ordinary skill in the art that other implantable devices can be used in place of stents.

The nozzle assembly 140, as will be discussed in further detail in conjunction with FIGS. 2-5, receives the polymer/drug solution (i.e., with or without solvent(s)) via the tubing 130*a* and the solvent via the tubing 130*b*. In addition, the nozzle assembly 140 receives high-pressure air from the atomizer 160. During a stent coating application process, the nozzle assembly 140 dispenses, via the nozzle tip 145, the polymer/drug solution and the solvent, which combines in situ, onto the stent 10. In other words, a pure solvent (e.g., about 90% to about 100% polymer and drug free) blends with the coating composition (i.e., polymer and/or drug composition with or without a solvent) out from the nozzle tip 145 before contacting the stent 10. It should be noted, therefore, that the coating composition should be formulated to compensate for the blending of the pure solvent with the composition. During the dispensing, high-pressure air from the atomizer 160 atomizes the combined polymer/drug solution and solvent, leading to a more uniform distribution on the stent 10.

It will be appreciated that the multiple control devices, i.e., the pump controls 110*a* and 110*b*, atomizer control 150, and mandrel control 185 can be combined into a single control device to simplify setting parameters for an operator.

FIG. 2 is a cross section illustrating a nozzle tip 145*a* of the coating system 100 (FIG. 1) in accordance with an embodiment of the invention. The nozzle tip 145*a* includes an atomizing air conduit 200*a*; a solvent feed conduit 210*a*; and a polymer/drug feed conduit 220*a*. In an embodiment of the invention, the air conduit 200*a*, the solvent feed conduit 210*a*, and the polymer/drug feed conduit 220*a* are concentrically positioned tubes, hypotubes, or syringes that run parallel to each other. The atomizing air conduit 200*a* is in communication with the atomizer 160 via the tubing 170 from which it receives atomizing air. The air conduit 200*a* circumscribes the solvent feed conduit 210*a*, which circumscribes the polymer/drug feed conduit 220*a*, and expels the atomizing air during a coating process so as to atomize the solvent and the polymer/drug expelled from the solvent feed conduit 210*a* and polymer/drug feed conduit 220*a* respectively. It will be appreciated by one of ordinary skill in the art that the polymer/drug feed conduit 220*a* can circumscribe the solvent feed conduit 210*a* instead of vice versa.

A tube 205*a* of the air conduit 200*a* has an inner diameter $d_{1_i}$ of about 0.0225 to about 0.45 inches and an outer diameter $d_{1_o}$ of about 0.0275 to about 0.50 inches (at the segment of the tube that is not bent). The tube 205*a* of the air conduit 200*a* is bent inwards to form an acute angle Φ of about 0 to about 60 degrees relative to a tube 215*a* of the solvent feed conduit 210*a* so as to bias the velocity of the exiting atomizing air towards the dispensed solvent and polymer/drug solution.

The tube 215*a* of the solvent feed conduit 210*a* has an inner diameter $d_{2_o}$ of about 0.0125 to about 0.20 inches and an outer diameter $d_{2_i}$ of about 0.0175 to about 0.25 inches and dispenses pure solvent. The solvent acts to prevent clogging of the polymer/drug feed conduit 220*a* by preventing accumulation of polymer and/or drugs on a tube 225*a* of the polymer/drug feed conduit 220*a*. The solvent mixes in situ with the dispensed polymer/drug when it is ejected out from the nozzle tip 145*a*. Since only a pure solvent is ejected from the solvent feed conduit 210*a*, the size of this conduit can be smaller than the size of the polymer/drug conduit 220*a*, which should be sized to allow for the ejection of a more viscous polymer and/or drug composition. In an embodiment of the invention, the tube 225*a*, as well as the tubes 205*a* and 215*a*, can each have an arcuate end, such as end 600 as shown in FIG. 6, to further prevent accumulation of polymer that may cause blockage. In addition, the tubes 205*a*, 215*a*, and 225*a* can be made of or coated with a non-stick material (e.g., TEFLON) to prevent accumulation of the polymer, which can lead to blockage.

The polymer/drug feed conduit 220*a* dispenses a polymer and/or drug from the polymer/drug reservoir 125*a* received via the tubing 130*a*. In an embodiment of the invention, the tube 225*a* of the polymer/drug feed conduit 220*a* has an inner diameter $d_{3_i}$ of about 0.0025 to about 0.05 inches and an outer diameter $d_{3_o}$ of about 0.0075 to about 0.10 inches.

FIG. 3 is a bottom view of the nozzle tip of the nozzle tip 145*a*. The polymer/drug feed conduit 220*a* is centered with the nozzle tip 145*a*. The solvent feed conduit 210*a* circumscribes the polymer/drug feed conduit 220*a*. The atomizing air conduit 200*a* circumscribes the solvent feed conduit 210*a*.

FIG. 4 is a cross section illustrating a nozzle tip 145*b* according to another embodiment of the invention. The nozzle tip 145*b* is substantially similar to the nozzle tip 145*a* and includes the same components. However, the tube 205*b* of the air conduit 200*b* does not extend to the same length as the tube 215*b* of the solvent feed conduit 210*b*, i.e., the air conduit tube 205*b* is shorter than the solvent feed conduit tube 215*b* by a distance X of, for example, up to about 0.2 inches. This nozzle tip 145*b* geometry substantially prevents any polymer clumping within the air conduit 200*b* since the tubes 215*b* and 225*b* extend out from the tube 205*b*.

FIG. 5 is cross section illustrating a nozzle tip 145*c* according to another embodiment of the invention. The nozzle tip 145*c* is substantially similar to the nozzle tip 145*a* and includes the same components. However, the polymer/drug feed conduit tube 225*c* is shorter than the solvent feed conduit tube 215*c* that circumscribes it, i.e., the polymer/drug feed conduit 220*c* is recessed within the solvent feed conduit 210*c* by a distance Y of, for example, up to about 0.2 inches. This nozzle tip 145*c* geometry substantially prevents any polymer clumping within the air conduit 200*c* and also ensures that the bottom of the tube 225*c* is swept clean with solvent from the solvent feed conduit 210*c*. It should also be noted that the tube 215*c* can also be recessed in the same extent as the tube 225*c* or be positioned such that the bottom of the tube 215*c* is between the bottom of the tubes 205*c* and 225*c*.

FIG. 6 is cross section illustrating a nozzle tip 145*d* according to a fourth embodiment of the invention. The nozzle tip 145*d* is substantially similar to the nozzle tip 145*a* and includes the same components. However, each of the tubes 205*d*, 215*d*, and 225*d* have arcuate ends, such as arcuate end 600. The arcuate ends of the tubes 205*d*, 215*d*, and 225*d* enable the solvent to contact more of the tubes' surface area, thereby prevent accumulation of the polymer on the tubes 205*d*, 215*d*, and 225*d*, which may lead to clogging of the nozzle tip 145*d*.

While particular embodiments of the present invention have been shown and described, it will be obvious to those skilled in the art that changes and modifications can be made without departing from this invention in its broader aspects. For example, the nozzle tip 145 can use internal mixing in place of external mixing. Therefore, the appended claims are to encompass within their scope all such changes and modifications as fall within the true spirit and scope of this invention.

What is claimed is:

1. A method of coating a stent, comprising:
    positioning a nozzle assembly relative to a stent, the nozzle assembly having a first tube for discharging a composition including a polymer, a second tube, positioned over the first tube, for discharging a solvent free or substantially free from drugs or the polymer, and a third tube, positioned over the second tube, for discharging a gas;
    discharging the composition and the solvent from the nozzle assembly onto the stent so that the discharged composition and discharged solvent combine before contacting the stent; and
    expelling the gas from the third tube so that the discharged solvent and the discharged composition are atomized by the gas into droplets,
    wherein the first tube and the second tube are in a recessed position inside of the third tube.

2. The method of claim 1, wherein the solvent and the composition are discharged at different rates.

3. The method of claim 1, wherein the composition additionally includes a drug.

4. The method of claim 1, wherein the first tube is centered relative to the second tube, and the second tube is centered relative to the third tube.

5. The method of claim 1, wherein the third tube includes a rim adjacent an outlet of the third tube, the rim having a side oriented at an angle towards the first tube and the second tube to cause the gas to be discharged towards the discharged solvent and the discharged composition.

6. The method of claim 1, wherein discharging the composition and the solvent includes preventing the composition from accumulating on each of the tubes during the coating process, and wherein each of the tubes has an arcuate end.

7. The method of claim 1, further comprising preventing the polymer discharged from the first tube from clumping within the third tube, and wherein a segment of the second tube is disposed between an outlet of the first tube and an outlet of the third tube.

8. The method of claim 1, wherein the tubes are made from or coated with TEFLON.

9. A method of coating a stent, comprising:
    discharging a composition including a polymer out from an end segment of a first tube and toward a stent;
    discharging a solvent out from an end segment of a second tube, the solvent being free or substantially free from drugs or the polymer, the end segment of the second tube disposed adjacent the end segment of the first tube such that the discharged composition and the discharged solvent combine before contacting the stent; and
    discharging gas out from an aperture formed in a third tube, the aperture having an annular shape that surrounds the end segment of the first tube and the end segment of the second tube such that the discharged composition and the discharged solvent are atomized by the discharged gas,
    wherein the end segment of the first tube and the end segment of the second tube do not extend out of the aperture of the third tube.

10. The method of claim 9, wherein the solvent and the composition are discharged at different rates.

11. The method of claim 9, wherein the composition additionally includes a drug.

12. The method of claim 9, wherein the end segment of the first tube is concentrically positioned inside the end segment of the second tube, and the end segment of the second tube is concentrically positioned inside the aperture of the third tube.

13. The method of claim 9, wherein the end segment of the first tube and the end segment of the second tube are disposed inside the third tube.

14. The method of claim 9, wherein the third tube includes a side adjacent the aperture formed in the third tube, the side oriented at an angle relative to the end segment of the first tube and the end segment of the second tube to cause the gas to be discharged towards the discharged solvent and the discharged composition.

15. The method of claim 9, further comprising preventing the composition discharged from the first tube from accumulating on the each of the tubes during the coating process, and wherein each of the tubes has an arcuate end.

16. The method of claim 9, further comprising preventing the composition discharged from the first tube from clumping within the third tube, and wherein the end segment of the second tube is disposed between the end segment of the first tube and the aperture formed in the third tube.

* * * * *